United States Patent [19]
Snow et al.

[11] Patent Number: 5,414,135
[45] Date of Patent: May 9, 1995

[54] VINYL SULFONE COUPLING OF POLYOXYALKYLENES TO PROTEINS

[75] Inventors: Robert A. Snow, West Chester; David L. Ladd, Wayne, both of Pa.

[73] Assignee: Sterling Winthrop Inc., Malvern, Pa.

[21] Appl. No.: 153,553

[22] Filed: Nov. 16, 1993

Related U.S. Application Data

[63] Continuation of Ser. No. 815,722, Dec. 30, 1991, abandoned.

[51] Int. Cl.$^6$ .................. C07C 315/04; C07C 317/04
[52] U.S. Cl. ........................................ 568/29; 568/30; 568/31; 568/32; 568/33
[58] Field of Search ............... 568/30, 32, 33, 29, 568/31

[56] References Cited

U.S. PATENT DOCUMENTS

| | | | |
|---|---|---|---|
| 4,179,337 | 12/1979 | Davis et al. | 435/181 |
| 4,251,626 | 2/1981 | Minamizono et al. | 430/527 |
| 4,732,836 | 3/1988 | Tomasi et al. | 436/547 |

FOREIGN PATENT DOCUMENTS

| | | | |
|---|---|---|---|
| 0200467 | 4/1985 | European Pat. Off. | |
| 0210761 | 7/1985 | European Pat. Off. | |
| 0236987 | 6/1987 | European Pat. Off. | |
| 3114043 | 5/1991 | Japan | 568/32 |

OTHER PUBLICATIONS

Journal of Biological Chemistry, vol. 257, No. 19, pp. 11443–11447 (1982) Cudd, A., Fridovich, I., "Electrostatic Interactions in the Reaction Mechanism of Bovine . . ."
Cancer Biochem. Biophys., 1984, vol. 7. pp. 175–186. Abuchowski, A., "Cancer Therapy with Chemically Modified Enzynes."
Tetrahedron 40, 1984, pp. 1581–1584, "Synthesis of Monomethoxy polyoxyettufene-Bound Hemoglobins", Leonard, M, Dellacherie, E.
Eur. Polym. J., vol. 19, No. 12, pp. 1177–1183 (1983) Zalipsky, S., Gilon, C., Zilkha, A., "Attachment of Drugs to Polyethylene Glycols".
Biochimica et Biophysica Acts, 791, (1984) pp. 219–225 Leonard, M. and Dellacherie, E., "Acylation of Human Hemoglobin with Polethylene: Derivatives".
Master of Science Thesis, "Modification of Proteins with Activated Polyethylene Glycols" Rutgers University, New Brunswick, N.J., USA (Oct. 1985) Kazo, G. M.
Journal of Pharmacy and Pharmacology, 35, pp. 757–758 (1983) Veronese, F. M., boccu, E. Schaivon, O., Velo, G. P., Conforti, A. Franco, L.

*Primary Examiner*—Johann Richter
*Assistant Examiner*—John Peabody
*Attorney, Agent, or Firm*—Liza D. Hohenschutz; William J. Davis

[57] ABSTRACT

A new class of polyalkylene oxide vinyl sulfone reagents is described. Also described are a method by which these reagents can be prepared as well as a method for using them in hydrated media for the modification of proteins. The novel polymer-to-protein conjugates made by reacting these reagents with proteins have advantages over similar conjugates prepared with prior art reagents in that they are more stable against hydrolysis and retain the positive charge carrying capacity at amine sites at which the modifying reagents are attached.

14 Claims, 1 Drawing Sheet

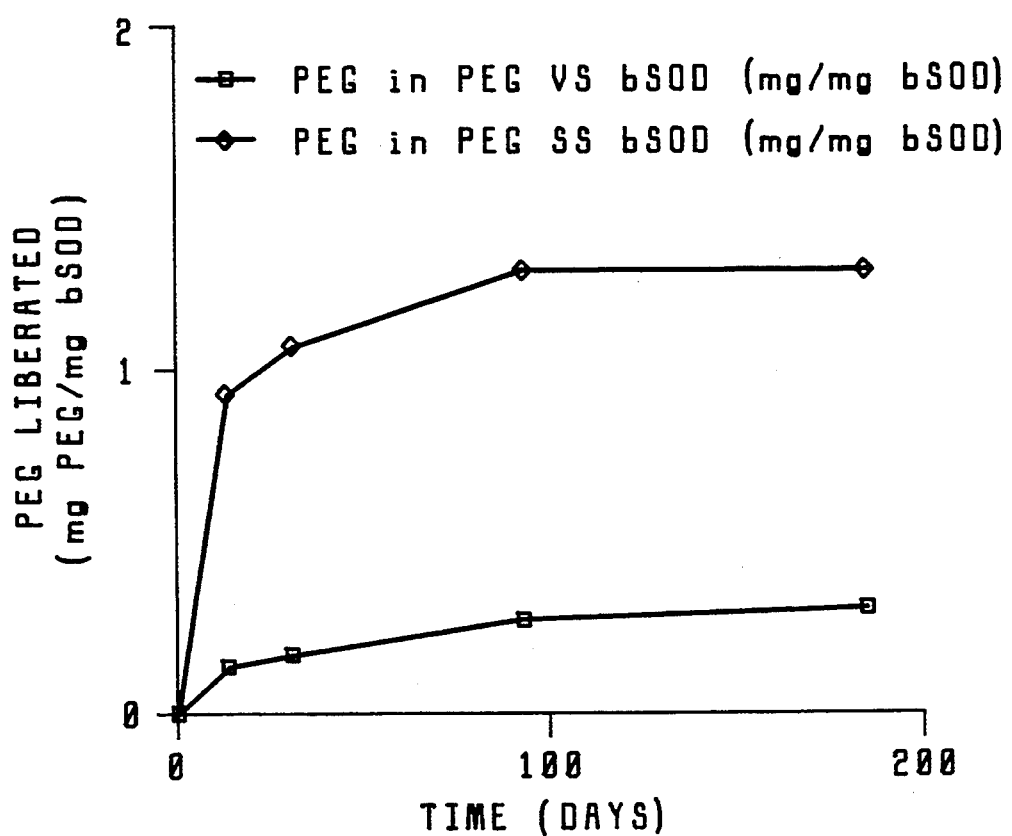

VINYL SULFONE COUPLING OF POLYOXYALKYLENES TO PROTEINS

This is a continuation of application Ser. No. 07/815,722, filed Dec. 30, 1991, now abandoned.

FIELD OF THE INVENTION

This invention relates to modification of proteins by functionalized polymeric materials for the purposes of increasing their effective half-lives in vitro and in vivo and of decreasing their in vivo immunogenic properties. In particular, this invention relates to polyalkylene glycols, for example, polyethylene glycol, coupled to proteins, such as bovine superoxide dismutase, recombinant human superoxide dismutase, interleukin-4, catalase, bovine growth hormone, thyrocalcitonin, and subtilisin, using vinyl sulfone coupling chemistry.

DESCRIPTION RELATIVE TO THE PRIOR ART

Chemical methods of conjugation of polymeric species to proteins frequently employ electrophilic functional groups that are chemically incorporated into the polymeric species in order to react with accessible nucleophilic functional groups which are inherently found in the protein structure as part of its amino acid composition. Examples of these nucleophilic groups include the epsilon amino group in lysine, the terminal alpha amino group of an amino acid located at the end of a peptide, and, less frequently found as such because of its facile tendency to be oxidized, the sulfhydryl group in cysteine. The latter amino acid, when situated in a sterically accessible site on the surface of a protein or of a protein fragment, is often found in nature to be oxidized in the form (together with a sulfhydryl group of a cysteine in another portion or fragment of the protein) of a sulfur-sulfur bond, which can serve to fix a particular molecular conformation or to cross-link two fragments of a protein. Amino groups such as those mentioned above, when situated on the surface of a protein do not suffer from this tendency to be oxidatively dimerized with each other, and are thus more freely and more commonly found to be available to react with electrophilic reagents. Nevertheless, it is possible, if so desired, to produce and isolate cysteine-containing proteins in a non oxidizing medium. In addition, it is possible to chemically regenerate free, surface-accessible, nucleophilic sulfhydryl groups on the surface of oxidized proteins by reduction of the sulfur-sulfur bonds to thereby provide sites of attachment by polymer bound electrophilic groups. In many cases, it is possible to retain desired biological properties of the protein or protein fragment upon reduction.

Known methods of electrophilic modification by polymeric materials of more commonly available amino groups on the surface of a protein result in the conversion of those amines into amides or pseudoamides. The amines are usually cationically charged in the native protein as a result of protonation under normal physiological pH conditions, and such protonation often contributes to the overall conformational stability and activity of the protein. However, the amide nitrogens of the thus converted protein amines of the (prior art) polymer conjugated proteins are not protonated under physiological conditions. These formerly amino nitrogens thus lose their capacity to contribute to the stability of the conformation of the protein and to the activity of the protein.

For example, it has been shown by Cudd, A. and Fridovich, I. in the *Journal of Biological Chemistry*, Vol 257, No. 19, pp 11443-11447 (1982) that superoxide anion, the substrate of the proteinaceous enzyme superoxide dismutase, exhibits an interaction with the net anionically charged enzyme which is assisted by the positive charges on the protonated lysine residues, and that elimination of the positive charges on the lysine residues of the enzyme by acylation suppresses activity. Additionally, polyethylene glycol activated ester reagents such as methoxypolyethyleneglycol succinimidyl succinate [(see, e.g., Abuchowski, A. et al, *Cancer Biochem. Biophys.*, 1984, Vol. 7, pp 175-186; and Leonard, M. and Dellacherie, E. (1984) *Tetrahedron*40, 1581-1584; ) and commercially available from Sigma Chemicals (1990 catalog number M3152)] that have been used in the acylation of protein amines [see, e.g., Zalipsky, S., Gilon, C., and Zilkha, A., *Eur. Polym. J.* Vol. 19, No. 12, pp 1177-1183 (1983); Leonard, M. and Dellacherie, E., *Biochimica et Biophysica Acta*, 791 (1984) 219-225; Kazo, G. M., Master of Science Thesis entitled "Modification of Proteins with Activated Polyethylene Glycols", Rutgers University, New Brunswick, N.J., U.S.A., October, 1985; and Tomasi, T. B. and Anderson, W. L., U.S. Pat. No. 4,732,863, issued Mar. 22, 1988] are very susceptible to hydrolysis and must-be prepared and stored under anhydrous conditions before being employed in protein modifications.

U.S. Pat. No. 4,179,337 (of Frank Davis, Theodorus Van Es, and Nicholas C. Palczuk) discloses the use of polyethylene glycol or polypropylene glycol coupled to proteins to provide a physiologically active non-immunogenic water soluble polypeptide composition in which the polyethylene glycol serves to protect the polypeptide from loss of activity without inducing substantial immunogenic response. The methods described in the patent for the coupling of polyethylene glycol to a protein involve either the conversion of a protein amino group into an amide or pseudoamide, with consequent loss of charge carrying capacity of the amino group (as discussed above), or the introduction at the amino group of the protein, or vicinal to it, of a heteroatom substituent such as a hydroxyl group or of a ring system that is not repeated in the polymer backbone.

European Patent Application 0 200 467 of Anjinomoto, Inc. describes superoxide dismutase that is chemically modified by a poly(alkylene oxide) which is functionalized at both ends of the polymer with activated carboxyl coupling groups, each capable of reacting with protein. These polymers are capable of reacting at both ends to cross-couple with proteins to form copolymers between the protein and the poly(alkylene oxide). Such copolymers do not have well defined or molecularly stoichiometric compositions.

European Patent Application 0 210 761 of Takeda Chemical Industries, Ltd. describes a superoxide dismutase which is modified by a 1,3,5-triazine substituted by two polyethylene glycol polymers. The triazine is attached to an amino group of the protein and thus converts it to a pseudoamide.

European Patent Application 0 236 987 of Takeda Chemical Industries, Ltd. describes the modification of superoxide dismutase by poly(alkylene oxide) imidoesters, i.e., imino esters or imidates. These materials must be prepared and stored under anhydrous conditions, and they react with protein at amino sites to convert the amines into amidines.

veronese, F. M., Boccu, E., Schaivon, O., Velo, G. P., Conforti, A., Franco, L., and Milanino, R., in *Journal of Pharmacy and Pharmacology*, 35, 757–758 (1983), reported that when bovine erythrocyte derived superoxide dismutase is modified with a polyethylene glycol carboxylic acid N-hydroxysuccinimide active ester, the half life of the enzyme in rats is increased over that of the unmodified protein. However, this active ester is very susceptible to hydrolysis and forms amide bonds with lysine epsilon amines on the protein.

There is, thus, a definite need in the art for a class of relatively hydrolytically stable, activated polymer-to-protein coupling reagents that will not only react with sulfhydryl groups if present and accessible on the surface of a protein, but also will form relatively stable coupling linkages to amine groups on accessible surfaces of proteins while maintaining the ability of those amine nitrogens to be positively charged under physiological conditions.

U.S. Pat. No. 4,251,626, assigned to Fuji Photo Film Co, Ltd.,("'626 patent") discloses a gelatin-reactive surface modifying agent having at least one long chain hydrophobic group on an alpha-quaternary ammonium-omega-vinyl sulfone substituted polyether which allegedly imparts improved antistatic property to photographic materials. A structure given in the patent is:

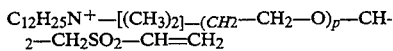

wherein p=9.

The patent requires that a quaternary nitrogen terminal group, having an alkyl group containing in the range of 8 to 18 carbons attached to the nitrogen, be attached to the terminus of a polyoxyethylene chain. By contrast, in the reagent of the present invention, an ether (e.g., alkoxy) terminal group is attached to the terminus of a polyoxyalkylene (e.g., polyoxyethylene) chain. The sulfone-containing surface modifying agent of the '626 patent was applied to gelatin for the sole purpose of imparting antistatic properties to the gelatin. The patent contains no suggestion to attach such antistatic surface modifying agents to specific protein compositions that could be used for therapeutic purposes. In fact, it is believed that use of the quaternary ammonium terminated agents of the '626 patent for modifying therapeutic proteins would impart immunogenic properties to the modified protein.

SUMMARY OF THE INVENTION

We have discovered that a polyalkylene oxide (PAO) comprising chains of PEO of varying molecular weight, containing at least one hydroxyl group, such as a polyethylene glycol (PEG), which may itself be a monoalkyl ether (for example, PEG monomethyl ether), can be activated and reacted with a difunctional sulfone such as a divinyl sulfone to provide a polymeric reagent comprising polyalkylene oxide chains [such as a polyethylene glycol (PEG)] of differing molecular weights each distinct chain or molecule of that distribution being attached to only one site of that difunctional sulfone. The other active site of the difunctional sulfone is capable of reacting with an amine group or a sulfhydryl group of a protein. Alternatively, the active site can be converted into a functional group, such as a vinyl group, that is capable of reacting with an amine group or a sulfhydryl group of a protein. In the practice of this invention, the polymer-to-sulfone monoadduct that contains a functional group capable of reacting with amine or sulhydryl groups of proteins can be isolated free of any unreacted starting difunctional sulfone. The adduct can be characterized spectroscopically, stored for a period of time, and then reacted (either as a single molecular weight distribution of reagent alone or in combination with higher or lower molecular weight distributions of reagents of this invention employed concomitant or sequentially with one another) with a protein to form a PAO-to-sulfone-to-protein conjugate. When the difunctional sulfone is divinyl sulfone and the polyalkylene oxide is polyethylene glycol monomethyl ether, the isolated intermediate is the one-to-one adduct, alpha-methoxypolyethylene glycol omega-2-(vinylsulfonyl)ethyl ether. Furthermore, the thus produced material can react with various proteins whereby to achieve the objectives and advantages of this invention.

The present invention provides novel polymeric reagents for the modification of proteins, The invention also provides novel polymer-to-protein conjugates prepared with the reagents of this invention. The polymer-to-protein conjugates of the present invention have a substantial capacity to resist hydrolysis at the polymer-to-protein coupling site. The novel reagents of the present invention modify accessible amine groups on proteins in Such a way as to maintain the positive charge carrying capacity of such amine groups. The novel reagents of the present invention modify accessible sulfhydryl groups on proteins. The polymer-to-protein conjugates of the present invention can be useful as pharmaceutical agents or drugs for the treatment of human or animal ailments.

It is an advantage of this invention that the novel polymeric reagents for the modification of proteins can be stored for a prolonged period of time without loss of activity toward proteins. It is another advantage of this invention that the novel polymeric reagents of this invention will react with proteins in aqueous media. It is another advantage of this invention that the novel polymeric reagents can be prepared in the presence of water, and will not themselves react substantially with water in the time it takes them to react with the protein. It is another advantage of this invention that proteins which are modified by the novel polymeric reagents of this invention exhibit increased circulating half lives in the blood with respect to the corresponding unmodified proteins. It is another advantage of this invention that the proteins that are modified by the novel polymeric reagents of this invention exhibit reduced antigenicity with respect to the corresponding unmodified proteins.

BRIEF DESCRIPTION OF THE FIGURE

The sole FIGURE depicts the relative amounts of PEG liberated with time at pH 0.7 PBS from PEG linked to bovine SOD through a vinyl sulfone linkage and through a succinate ester linkage.

DETAILED DESCRIPTION OF THE INVENTION

In one aspect, the present invention comprises a novel polyalkylene oxide vinyl sulfone reagent (such as, for example, a polyethylene glycol vinyl sulfone reagent) for the modification of proteins (which modified proteins are useful as pharmaceutical agents or drugs). In another aspect, the invention provides a method for the preparation of the novel vinyl sulfone reagent of the invention in high yield in a reaction medium which may contain water. In yet another aspect, the invention provides a method for the preparation of novel protein adducts of the reagents in aqueous medium. In yet another aspect, the invention provides novel polypeptide, preferably protein, adducts in which the reagent of the invention is attached to available free sulfhydryl sites and amine sites of the protein, which amine sites retain their inherent capacity to be protonated under physiological conditions. In addition, the polymer-to-protein adducts of the invention have excellent hydrolytic stability.

The polyalkylene oxide vinyl sulfone reagent of the invention is prepared by reacting a polyalkylene oxide moiety with a reagent that contains a sulfone functional group or a precursor thereto. The sulfone in the resulting reagent activates an adjacent functional group for coupling to a protein. Such coupling of the reagent of the invention to the protein produces the modified proteins of the present invention.

Preferably, the novel reagent of the invention is prepared by reacting a polyalkylene oxide (or an activated polyalkylene oxide) having a molecular weight in the range of 250 to 200,000 daltons with a reagent containing a vinyl sulfone functionality (or a precursor thereof) to form a vinyl sulfone ether monoadduct of the polyalkylene oxide. A reaction scheme illustrating a presently preferred embodiment is:

$$CH_3O-(CH_2-CH_2-O)_n-CH_2-CH_2-OH \quad + \quad CH_2=CH-SO_2-CH=CH_2$$

$$\downarrow \text{NaOH} \atop \text{THF/H}_2\text{O}$$

$$CH_3O-(CH_2-CH_2-O)_n-CH_2-CH_2-O-CH_2-CH_2-SO_2-CH=CH_2$$

Preferably, the polyalkylene oxide is a polyalkylene oxide monoalkyl ether, preferably a polyalkylene oxide monomethyl ether, and most preferably a polyethylene glycol monomethyl ether (as represented in the foregoing reaction scheme). The activated polyalkylene oxide is preferably an alkoxide or a halide derivative or an activated ester derivative thereof.

The average molecular weight of the polyalkylene oxide used to prepare the reagent of the invention is in the range of 250 to 200,000 daltons, preferably in the range of 250 to 100,000 daltons, more preferably in the range of 2,000 to 20,000 daltons, most preferably in the range of 2,000 to 10,000 daltons.

The reagent containing the sulfone group (or a precusor thereof) that is reacted with the polyalkylene oxide or activated polyalkylene oxide to form the polyalkylene oxide vinyl sulfone reagent of the present invention is represented by the formula:

$$X_x-E-S(=O)_f-A_a-B_b-L-D_d$$

where:
X is a leaving group, preferably a halogen such as chlorine, bromine, or iodine, or a sulfonate ester group,
x is zero or one,
E is hydrogen, or an alkylene group of 1 to 8 carbons, or an alkylenyl group of 2 to 8 carbons, preferably an ethylenyl group, or a substituted aryl group of the formula $$G-(C_6.H_h.R^1_i)-$$

where:

G is a leaving group, preferably, a nitro group or a halogen such as fluorine or bromine or chlorine, or G is a vinyl group, or a haloalkyl group such as a chloromethyl or bromomethyl group, or a vinyl sulfone group, each $R^1$ is an electron withdrawing group independently selected from fluorine, trifluoromethyl, nitro, and functional equivalents thereof;
i is 0 or an integer from 1 to 4; and
h is (4-i);
f is zero, one or two;
A is an arylene or an aralkylene group of 6 to 8 carbons which may be unsubstituted or substituted with one or more low molecular weight substituents such as a halogen, methyl, methoxy, trifluoromethyl, and the like; or an alkylene radical of 1 to 8 carbon atoms which may be saturated or unsaturated and which may contain one or more heteroatoms such as an oxygen atom that is comprised in an ether or an ester group, or a sulfur atom that is comprised in a sulfide or a sulfone or a sulfoxide group, or a nitrogen atom as part of a heteroaromatic ring or an amide group;
a is zero or one;
B is a sulfur atom, a sulfone group, or a sulfoxide group;
b is zero or one;
L is an alkylenyl radical having from 2 to 10 carbon atoms, preferably ethylenyl, or an alkylene radical of 2 to 6 carbon atoms, preferably ethylene;
D is a leaving group, preferably a halogen, a sulfonate ester, an hydroxyl or a protected hydroxyl such as an ester or ether; and
d is zero or one;
when d is 0, L is $$\begin{array}{c} R^2 \\ | \\ -C=CH_2 \end{array}$$

when d is 1, L is $$\begin{array}{c} R^2 \\ | \\ -C-CH_2-; \\ | \\ R^3 \end{array}$$

$R^2$ is selected from H, F, Cl, $CF_3$ and alkyl groups of 1 to 8 carbon atoms;
$R^3$ is selected from H, and G (as defined above).
Preferably, the reagent containing the sulfone group is represented by the formula:

$$CH_2=CH-SO_2-A_a-B_b-L-D_d$$

where:
A, a, B, b, L, D and d are all as defined above.
More preferably, the reagent containing the sulfone group is represented by the formula:

$$CH_2=CH-SO_2-A_a-B_b-L-D_d$$

where:
A is an alkylene radical of 1 to 8 carbon atoms which may be saturated or unsaturated and which may contain one or more heteroatoms such as an oxygen atom, preferably in the form of an ether group;
a is zero or one;
B is a sulfoxide group or a sulfone group;
b is zero or one;
L is as defined above;
D is as defined above; and
d is zero or one.

Yet more preferably, the reagent containing the sulfone group is a bis(vinyl sulfone) reagent represented by the formula:

$$CH_2=CH-SO_2-A_aB_b-CH=CH_2$$

where:
A is an alkylene radical of 1 to 8 carbon atoms which may be saturated or unsaturated and which may contain one or more heteroatoms, such as an oxygen atom preferably in the form of an ether group;
a is zero or one;
B is a sulfoxide or a sulfone group; and
b is zero or one.

The presently preferred reagent containing the sulfone group that is reacted with the polyalkylene oxide (to form the polyalkylene oxide vinyl sulfone reagent of the present invention) is divinyl sulfone:

$$CH_2=CH-SO_2-CH=CH_2$$

The preferred method for the preparation of the polyalkylene oxide vinyl sulfone reagents of the present invention is to treat a solution of the polyalkylene oxide containing the hydroxyl group in a solvent such as tetrahydrofuran with the divinyl sulfone reagent in the presence of a catalytic quantity [e.g. from about 1 mole percent to about 40 mole percent] of an aqueous base such as an aqueous solution of sodium hydroxide. The polyalkylene oxide vinyl sulfone reagent can be isolated by removal of the solvent, preferably by precipitation induced by admixing with an excess of a miscible nonsolvent such as ethyl ether. Any excess divinyl sulfone can be removed from the polyalkylene oxide vinyl sulfone reagent by washing the latter in a solvent for the divinyl sulfone such as ether in which solvent the reagent of the invention is not readily soluble.

The thus formed polyalkylene oxide vinyl sulfone reagents of the present invention are represented by the structural formula:

$$R_4-O-(PAO)-E-S(=O)_2-A_a-B_b-C(R^2)=CH_2$$

wherein:
$R_4$ is H or an alkyl or an aralkyl group of 1 to 8 carbon atoms which may be substituted with an alkoxy group of 1 to 3 carbon atoms;
PAO is a polyalkylene oxide having an average molecular weight in the range of 250 to 200,000 daltons; and
E, A, a, B, b, and $R^2$ are defined above.

In a preferred embodiment, the polyalkylene oxide vinyl sulfone reagents of the present invention are represented by the structural formula:

$$R_4-O-(PAO)-E-S(=O)_2-A'_a-B_b-C(R^2)=CH_2$$

wherein:
A' is an alkylene radical of 1 to 8 carbon atoms which may be saturated or unsaturated and which may contain one or more heteroatoms such as an oxygen atom in the form of an ether, or a sulfur atom in the form of a sulfoxide group; and
$R_4$, PAO, E, a, B, b, and $R^2$ are as defined above.

In a more preferred embodiment, the polyalkylene oxide vinyl sulfone reagents of the present invention are represented by the structural formula:

$$R_4-O-(PAO)-O-CH_2CH_2-S(=O)_2-A''_a-B_bC(R^2)=CH_2$$

wherein:
A'' is an alkylene radical of 1 to 8 carbon atoms which may be saturated or unsaturated and which may contain one or more heteroatoms such as an oxygen atom in the form of an ether, or a sulfur atom in the form of a sulfoxide group; and
$R_4$, PAO, a, B, b, and $R^2$ are as defined above.

In an even more preferred embodiment, the polyalkylene oxide vinyl sulfone reagents of the present invention are represented by the structural formula:

$$R_4-O-(PAO)-O-CH_2CH_2-S(=O)_2-A^2_a-B_b-C(R^2)=CH_2$$

wherein:
$A^2$ is a saturated alkylene radical of 1 to 8 carbon atoms and which may contain one or more heteroatoms such as an oxygen atom in the form of an ether, or a sulfur atom in the form of a sulfoxide group; and
$R_4$, PAO, a, B, b, and $R^2$ are as defined above.

In a yet more preferred embodiment, the polyalkylene oxide vinyl sulfone reagents of the present invention are represented by the structural formula:

$$R_4-O-(PAO)-O-CH_2CH_2-S(=O)_2-A^2_a-C(R^2)=CH_2$$

wherein:
$A^2$, $R_4$, PAO, a, and $R^2$ are as defined above.

In a yet more preferred embodiment, the polyalkylene oxide vinyl Sulfone reagents of the present invention are represented by the structural formula:

$$R_4-O-(PAO)-O-CH_2CH_2-S(=O)_2C(R^2)=CH_2$$

where:
$R_4$, PAO, and $R^2$ are defined above.

In a yet more preferred embodiment, the polyalkylene oxide vinyl sulfone reagents of the present invention are represented by the structural formula:

$$R_4-O-(PAO)-O-CH_2CH_2-S(=O)_2-CH=CH_2$$

wherein:
$R_4$ and PAO are defined above.

In a yet even more preferred embodiment, the polyalkylene oxide vinyl sulfone reagents of the present invention are represented by the structural formula:

$$R_4-O-(PAO)-O-CH_2CH_2-S(=O)_2-CH=CH_2$$

wherein:
PAO is a polyethylene glycol of molecular weight 250 to 200,000 daltons; and
$R_4$ is defined above.

In a yet more preferred embodiment, the polyalkylene oxide vinyl sulfone reagents of the present invention are represented by the structural formula:

$$R_4-O-(PAO)-O-CH_2CH_2-S(=O)_2-CH=CH_2$$

wherein:
PAO is a polyethylene glycol of molecular weight 250 to 100,000 daltons; and
$R_4$ is defined above.

In an even more preferred embodiment, the polyalkylene oxide vinyl sulfone reagents of the present invention are represented by the structural formula:

$$R_4-O-(PAO)-O-CH_2CH_2-S(=O)_2-CH=CH_2$$

wherein:
PAO is a polyethylene glycol of molecular weight 250 to 20,000 daltons; and
$R_4$ is defined above.

In an even more preferred embodiment, the polyalkylene oxide vinyl sulfone reagents of the present invention are represented by the structural formula:

$$R_4-O-(PAO)-O-CH_2CH_2-S(=O)_2-CH=CH_2$$

wherein:
PAO is a polyethylene glycol of molecular weight 2,000 to 10,000 daltons; and
$R_4$ is defined above.

In a presently preferred embodiment, the polyalkylene oxide vinyl sulfone reagents of the present invention are represented by the structural formula:

$$CH_3-(PAO)-O-CH_2CH_2-S(=O)_2-CH=CH_2$$

wherein:
PAO is a polyethylene glycol of molecular weight 2,000 to 20,000 daltons.

The presently most preferred polyalkylene oxide vinyl sulfone reagent of this invention, polyethylene glycol monomethyl mono[2-(vinyl sulfonyl)ethyl] ether having a molecular weight in the range of 2,000 to 10,000 daltons, can be isolated and stored and characterized as a discrete 1:1 adduct of the polyethylene glycol and divinylsulfone. It can then be reacted in aqueous medium with proteins containing amine groups, such as the epsilon amine of the amino acid lysine, as well as peptide terminal amine groups and, if present, accessible free sulfhydryl groups. The rate of addition of the reagent of this invention to free sulfhydryl groups can be shown to be faster than the rate of addition to amino groups, and this can be shown unequivocally using amino acids containing these functional groups as models for the proteins.

The polyalkylene oxide-(diethyl sulfone)-polypeptide (or protein) adducts [which are preferably methoxypolyethylene glycol-(diethyl sulfone)-protein adducts] thus formed are stable to hydrolysis at the reagent-to-protein coupling site for extended periods of time in aqueous solution. The polyalkylene oxide-(diethyl sulfone)-protein adducts of this invention also exhibit extended circulating half lives in the blood and are less immunogenic when compared to the unmodified proteins.

In general, in the polypeptide-polyalkylene oxide adducts of the present invention, the polypeptide or protein is bonded to one or more polyalkylene oxide moieties through a sulfone-containing group on each polyalkylene oxide. Preferably, the polypeptide is a protein, and the adduct has the structural formula:

$$\{[R_4-(PAO)-E-S(=O)_2-A_a-B_bC(R^2)H-CH_2]_r-Q\}_q\text{-protein}$$

wherein:
Q is a sulfur atom or nitrogen atom that is attached to the protein;
q is a positive integer;
r is one when Q is sulfur, and r is one or two when Q is nitrogen;
$R_4$ is H or an alkyl or an aralkyl group of 1 to 8 carbon atoms which may be substituted with an alkoxy group of 1 to 3 carbon atoms;
PAO is a polyalkylene oxide having an average molecular weight in the range of 250 to 200,000 daltons;
E is an alkylene group of 1 to 8 carbons, or an alkylenyl group of 2 to 8 carbons, preferably an ethylenyl group, or a substituted aryl group of the formula $$-(C_6H_hR^1{}_i)-$$

where:
each $R^1$ is an electron withdrawing group independently selected from fluorine, trifluoromethyl, nitro, and functional equivalents thereof;
i is 0 or an integer from 1 to 4, and
h is (4-i);
A is an arylene or an aralkylene group of 6 to 8 carbons which may be unsubstituted or substituted with one or more low molecular weight substituents selected from halogen, methyl, methoxy, and trifluoromethyl; or an alkylene radical of 1 to 8 carbon atoms which may be saturated or unsaturated and which may contain one or more heteroatoms selected from an oxygen atom comprised in an ether or an ester group, a sulfur atom comprised in a sulfide or a sulfone or a sulfoxide group, and a nitrogen atom that is part of a heteroaromatic ring or an amide group;
a is zero or one;
B is a sulfur atom, a sulfone group, or a sulfoxide group;
b is zero or one; and
$R^2$ is selected from H, F, Cl, $CF_3$ and alkyl groups of 1 to 8 carbon atoms.

More preferably, A is an alkylene radical of 1 to 8 carbon atoms which may be saturated or unsaturated and which may contain one or more heteroatoms such as an oxygen atom in the form of an ether, or a sulfur atom in the form of a sulfoxide group.

In a presently preferred embodiment, the adduct has the structural formula:

$$\{[R_4O-(PAO)-E-S(=O)_2-A'_a-B_bC(R^2)H-CH_2]_r-Q\}_q\text{-protein}$$

wherein:

A' is an alkylene radical of 1 to 8 carbon atoms which may be saturated or unsaturated and which may contain one or more heteroatoms selected from an oxygen atom in the form of an ether, or a sulfur atom in the form of a sulfoxide group (and Q, q, r, $R_4$, PAO, E, a, B, b and $R^2$ are as defined above). Preferably, $R_4$ is $CH_3$.

As indicated in the description of the vinyl sulfone reagent of the invention, it is preferred that POA be a polyethylene glycol having a molecular weight in the range of 250 to 200,000 daltons, more preferably 250 to 100,000 daltons, still more preferably 250 to 20,000 daltons, yet more preferably 2,000 to 10,000 daltons.

The following non-limiting examples will serve better to illustrate the practice of the present invention. The relatively higher molecular weight compounds of this invention contain a relatively large amount of polyalkylene oxide per vinyl sulfone group. To facilitate spectroscopic characterization of the vinyl sulfone functional groups in the relatively higher molecular weight compounds of this invention and to facilitate the elucidation of the structure of the protein adducts of the reagents of this invention, a number of relatively lower molecular weight homologous compounds were prepared to serve as models.

EXAMPLE 1

Preparation of a reagent of this invention comprising an adduct of triethylene glycol monomethyl ether with divinyl sulfone: Alpha-[2-(ethenyl-sulfonyl)ethyl]-omega-methoxy-triethyleneglycol. A solution of divinyl sulfone (8.295 mL, 0.0826 mol) and triethylene glycol monomethyl ether (4.576 mL, 0.0286 mol) in 143 mL of tetrahydrofuran (THF) was treated with 9.95 mL of 1.0N sodium hydroxide solution. After two hours at room temperature, 9.95 mL of 1.0 N hydrochloric acid solution were added. The THF solution was decanted from an oil phase and the solvent was removed by rotary evaporation. The residue was dissolved in water, and washed twice with ether; and the organic material was extracted into chloroform in two portions. The combined extracts were washed with water, dried over anhydrous magnesium sulfate, and filtered; and the solvent was evaporated. The residual oil was distilled under vacuum (b.p. 162°–177° C. at 0.7 mm) to give 4.04 g (50% yield) of product which exhibited the following $^1$H NMR spectrum in deuterochloroform ($CDCl_3$) consistent with the structure: 3.27 (t[triplet], 2H, oxyethylsulfonyl), 3.38 (s[singlet], 3H, methoxyl), 3.54 to 3.66 (m[multiplet], 12H, ethyleneoxyl), 3.91 (t, 2H, oxyethylsulfonyl), 6.09 (d[doublet], 1H, vinyl), 6.40 (d, 1H, vinyl), and 6.84 ppm (d of d[doublet of doublets], 1H, vinyl).

EXAMPLE 2

Preparation of a reagent of this invention comprising a 5,000 dalton polyethylene glycol monomethyl ether adduct of divinyl sulfone: Alpha-[2-(ethenyl- sulfonyl)ethyl]-omega-methoxy-poly(oxy-1,2-ethanediyl).

A solution of 17.23 g (3.307 mmol) of methoxypolyethylene glycol of average molecular weight 5210 daltons obtained from Union Carbide Corporation was prepared by dissolving the polymer in 172 mL of warm (40° C.) tetrahydrofuran (THF) under a nitrogen atmosphere with magnetic stirring. The solution was cooled to room temperature and then treated with 1.00 mL (9.92 mmol) of divinyl sulfone followed by 12.0 mL of 0.1N aqueous sodium hydroxide solution. The reaction mixture was stirred at ambient temperature for 5 h, then neutralized with 12.0 mL of 0.1N hydrochloric acid solution, and filtered. The filtrate was concentrated on a rotary evaporator with mild heating to remove most of the THF. The residual solution was diluted with 50 mL of water, washed three times with ether, and then extracted three times with chloroform. The combined chloroform extracts were then washed with water, dried over anhydrous magnesium sulfate, and filtered. The solvent was evaporated to leave a white solid which was then dissolved in 49 mL of methylene chloride. The product was precipitated by adding 550 mL of ether. The precipitated solid was filtered, washed with ether and then vacuum dried to yield 13.92 g (79%) of desired product which exhibited a proton NMR spectrum which was similar to that of the compound prepared in Example 1 except for a larger signal for the ethylene oxide protons, and which is consistent with the desired structure: $^1$H NMR ($CDCl_3$), 3.27 (t, 2H, oxyethylsulfonyl), 3.38 (s, 3H, methoxyl), 3.54 to 3.66 (m, with an intense singlet [approximately 450H] at 3.70 ppm, polyoxyethylenyl), 3.91 (t, 2H, oxyethylsulfonyl), 6.09 (d, 1H, vinyl), 6.40 (d, 1H, vinyl), and 6.84 ppm (d of d, 1H, vinyl).

EXAMPLE 3

Preparation of a reagent of this invention comprising a 10,000 dalton polyethylene glycol monomethyl ether adduct of divinyl sulfone: Alpha-[2-(ethenyl- sulfonyl)ethyl]-omega-methoxy-poly(oxy-1,2-ethanediyl).

This material was prepared according to the method described in Example 2 in 78% yield from 0.397 mL of divinyl sulfone and 12.73 g of methoxypolyethy glycol with an average molecular weight of 9666 daltons. It exhibited a proton NMR spectrum in $CDCl_3$ substantially similar to that observed in the product of Example 2 with respect to the position and relative intensities of the resonances of the methoxyl, vinyl, and oxyethylsulfonyl protons to one another as well as to the position of the polyethyleneoxy protons, whose resonance intensity was greater than those in the spectrum of Example 2.

EXAMPLE 4

Preparation of a reagent of the invention comprising a 2,000 dalton polyethylene glycol monomethyl ether adduct of divinyl sulfone: Alpha-[2-(ethenyl- sulfonyl)ethyl]-omega-methoxy-poly(oxy-1,2-ethanediyl).

This material was prepared according to the method described in Example 2 in 81% yield from 0.871 mL of divinyl sulfone and 6.09 g of methoxypolyethylene glycol with an average molecular weight of 2105 daltons. It exhibited a proton NMR spectrum substantially similar to that observed in the product of Example 2 with respect to the position and relative intensities of the resonances of the methoxyl, vinyl, and oxyethylsulfonyl protons to one another as well as to the position of the polyethyleneoxy protons, whose resonance intensity was reduced with respect to that in the spectrum of Example 2.

EXAMPLE 5

Modification of recombinant human interleukin-4 (rhuIL-4) with 10,000 dalton alpha-[2-(ethenylsulfonyl)ethyl]-omega-methoxy-poly(oxy-1,2-ethanediyl). A solution of rhu-IL4 (76 $\mu$L of a 5.26 mg/ml solution in 100 mM aqueous Tris [tris(hydroxymethyl)aminomethane] buffer; equivalent to 400 μg of protein) was combined with 18 μL of a 156 mg/ml solution in Dulbecco's phosphate buffered saline of alpha-[2-(ethenylsulfonyl)ethyl]-omega-methoxy-poly(oxy-1,2ethanediyl) prepared as described in Example 3. The solution was held at 37° C. for 21 h. The reaction product was analyzed by size exclusion HPLC on a Bio-Sil SEC-250 column, eluting with phosphate buffered saline. The reaction product was observed to be a mixture of starting native rhu-IL-4 (with a retention time of 17.5 minutes) plus three new peaks with retention times at 12.6, 10.8, and 6.3 minutes, respectively). The peak with the longest retention time (12.6 minutes) was isolated by HPLC, and was shown by gel electrophoresis to be a single broad band of polyethylene glycol-conjugated IL-4 free of native protein. The in vitro activity of the PEG (vinyl sulfone) conjugated IL-4 was shown to be indistinguishable from that of the native IL-4 in a tonsil B-cell bioassay.

EXAMPLE 6

Modification of recombinant human interleukin-4 (rhuIL-4) with 5,000 dalton alpha-[2-(ethenylsulfonyl)ethyl]-omega-methoxy-poly(oxy-1,2-ethanediyl).

A solution of rhu-IL4 (8 μL of a 12.4 mg/ml solution in 100 mM Tris; equivalent to 100 μg of protein) was combined with 13.4 μL of 0.1M sodium borate buffer, pH 8.5 and 6 μL of a 170 mg/ml aqueous solution of alpha-[2-(ethenylsulfonyl)ethyl]-omega-methoxy-poly(oxy-1,2-ethanediyl) prepared as described in Example 2. The solution was held at room temperature for 29 h, then quenched with 10 μL of 2M glycine and diluted with 100 μL of phosphate buffered saline (PBS). The modified protein was purified by size exclusion HPLC on a Shodex WS 803 column, eluting with PBS in a fashion similar to that used in Example 5. The modified protein with the longest retention time was characterized by gel electrophoresis as above, and its in vitro activity was indistinguishable from that of the native protein in a tonsil B-cell assay.

EXAMPLE 7

Modification of bovine catalase (bCAT) with 5,000 dalton alpha-[2-(ethenylsulfonyl)ethyl]-omega-methoxy-poly(oxy-1,2-ethanediyl).

To 0.75 mL of a solution of catalase (Sigma, lot 87F-7010) in a sterile Centricon 30 microconcentrator was added 1.0 ml of a 0.1 M pH 8.5 sodium borate solution. The resulting enzyme solution was centrifuged for 25 min at 4° C. and then reconstituted to 1.00 ml volume with the 0.1M pH 8.5 borate buffer. The enzyme solution was then added to a solution of 225 mg of alpha-[2-(ethenylsulfonyl)ethyl]-omega-methoxy-poly(oxy-1,2-ethanediyl) that was prepared as described in Example 2 in 2.0 mL of the above buffer. The solution was capped and heated for 20 h at 37° C. The reaction product solution was placed into two Centricon 30 microconcentrators and the product was washed by centrifugation with several volumes of phosphate buffered saline at about 4° C. Twelve mL of filtrate was collected, and the retentate was filtered through a 0.2 μm filter to give a solution containing 3.485 mg/ml of PEG modified protein. (The estimated protein content as determined by HPLC was approximately 3.24 mg/ml.) When compared both separately and as an admixture of product and starting material after isolation of the product, the PEG modified protein exhibited a shorter retention time than did the native unmodified protein in size exclusion HPLC.

EXAMPLE 8

Modification of the protease Subtilisin Carlsberg with 5,000 dalton alpha-[2-(ethenylsulfonyl)ethyl]-omega-methoxy-poly(oxy-1,2-ethanediyl).

A solution of 894 mg of alpha-[2-(ethenylsulfonyl)ethyl]-omega-methoxy-poly(oxy-1,2-ethanediyl), prepared as described in Example 2, in 4.47 mL of 0.1M sodium borate buffer at pH 9.0 was added to 112 mg of solid Subtilisin Carlsberg. The enzyme was dissolved therein with the aid of an ultrasound bath, and the reaction mixture was then heated for 22 hours at 37° C. To this solution was then added 1.12 mL of a 0.5M aqueous Gly-Gly solution; then the reaction mixture was stirred at ambient temperature overnight and then diafiltered versus phosphate buffered saline using an Amicon stirred cell device and a YM30 membrane. The retentate was analyzed by HPLC on a Shodex WS 803 column using Dulbecco's phosphate buffered saline as the mobile phase at 0.75 ml/min. Native subtilisin Carlsberg had a retention time of 15.7 minutes, while the adduct which was isolated had a retention time of 11.0 minutes.

Example 9

Modification of bovine superoxide dismutase (bSOD) with a 5,000 dalton alpha-[2-(ethenylsulfonyl)ethyl]-omega-methoxy-poly(oxy-1,2-ethanediyl).

A solution of bovine superoxide dismutase with in vitro specific activity of 3960±500 Units/mg (at pH 7.8 and 25° C.) measured according to the assay described by McCord and Fridovich, *J. Biol. Chem.*, 244, pp 6049–605, was prepared by dissolving 159 mg (5.10 μmol) of enzyme in 10.6 mL of 0.1M sodium borate buffer, pH 8.5. The enzyme solution was then treated with a solution of 700 mg (131 μmol) of alpha-[2-(ethenyl-sulfonyl)ethyl]-omega-methoxy-poly(oxy-1,2-ethanediyl), prepared as described in Example 2 in 0.35 mL of water. The reaction mixture was stirred at room temperature for 41.5 h, then filtered through a 0.22 μm filter. The filtered solution was then diafiltered against PBS using an Amicon diafiltration apparatus with an YM-30 ultrafiltration membrane. The diafiltered solution was filtered again through a 0.22 μm filter giving 10.56 g of solution containing 14.0 mg/ml of protein (93% recovery). Hydrophobic interaction HPLC using a Bio-Rad Bio-Gel Phenyl-5-PW column with a 100 to 0% ammonium sulfate gradient showed a single peak with retention time of 14.6 min versus that of native SOD of 7.5 min. The modified enzyme exhibited a specific activity of 3070 Units/mg.

Example 10

Modification of recombinant human superoxide dismutase (rhuSOD) with 5,000 dalton alpha-[2-(ethenylsulfonyl)ethyl]-omega-methoxy-poly(oxy-1,2-ethanediyl).

A 1.80 mL aliquot of a 43.1 mg/ml solution of rhu-SOD having a specific activity of 2700 Units/mg (equivalent to 77.6 mg, 2.43 μmol of enzyme) was treated with a solution prepared from 338 mg (63.4 μmol) of 5,000 dalton molecular weight alpha-[2-(ethenylsulfonyl)ethyl]-omega-methoxy-poly(oxy-1,2-ethanediyl) prepared in Example 2 and 3.357 mL of 0.1M sodium borate buffer, pH 8.5. The reaction mixture was stirred at room temperature for 45 h, then worked up as described in Example 9 to yield 5.72 g of solution containing 12.4 mg/ml of protein (92% recovery). The enzyme exhibited a specific activity of 2670 Units/mg, and displayed a change in HPLC retention time from that of the unmodified enzyme similar to that seen in Example 9.

Example 11

Preparation of a methoxypolyethylene glycol succinimidyl succinate adduct of bovine superoxide dismutase (prior art method and product for use in the comparative in vitro stability studies of Example 12).

The method of Kazo [see Kazo, G. M., Master of Science Thesis entitled "Modification of Proteins with Activated Polyethylene Glycols", Rutgers University, New Brunswick, N.J., U.S.A., October, 1985] employing methoxypolyethylene glycol succinimidyl succinate [prepared according to the method of Abuchowski (see Abuchowski, A. et al, *Cancer Biochem. Biophys.* 1984, Vol 7, pp 175–186] and bovine superoxide dismutase (EC 1.15.1.1) (bSOD) with a specific activity of 3780 Units/mg in pH 7.8 phosphate buffer was used to prepare a solution of polyethylene glycol succinate-conjugated bSOD. The product solution was examined for homogeneity by reverse phase HPLC using a Brownlee BU-G03 C4 column monitored at 214 nm, by PAGE electrophoresis using a Pharmacia Phast system with silver staining development, and by size exclusion HPLC (TSK 3000 PWXL column) using refractive index detection. Solution protein content was determined by the biuret method. The per cent modification was determined by titration with trinitrobenzenesulfonic acid and found to be 55%. Size exclusion HPLC retention time of the unmodified enzyme was 17.46 minutes while the retention time of the modified enzyme was 10.31 minutes. After a 0.22 micron filtration, the enzyme solution was diafiltered against 50 mM sodium phosphate containing 0.85% NaCl at pH 7.0 for 10 volume passes. The resulting solution was filtered through a 0.22 micron Millex-GV filter and placed in 15 vials (0.7 ml fill) under sterile conditions. Kimble 2 ml USP type I vials, West 13 mm 4416/50 gray teflon coated butyl stoppers, and West 13 mm FO Lacq crimp tops were used. The final concentration of protein was 10.55 mg/ml.

EXAMPLE 12

Comparison of the hydrolytic stability of the bovine superoxide dismutase adduct of 5,000 dalton methoxypolyethylene glycol succinimidyl succinate of Example 11, with the adduct of the invention prepared in Example 9, i.e. the adduct of bovine superoxide dismutase with 5,000 dalton alpha-[2-(ethenylsulfonyl)ethyl]-omega-methoxy-poly(oxy-1,2 -ethanediyl).

A solution of protein conjugate prepared according to Example 9 (PEG vs bSOD) was subjected to an additional 0.22 micron filtration, and then the enzyme solution was diafiltered against 50 mM sodium phosphate containing 0.85% NaCl at pH 7.0 for 10 volume passes. The resulting solution was filtered through a 0.22 micron Millex-GV filter and placed in 15 vials (0.7 ml fill) under sterile conditions. Kimble 2 ml USP type I vials, West 13 mm 4416/50 gray teflon coated butyl stoppers, and West 13 mm FO Lacq crimp tops were used. The final concentration of protein was 8.87 mg/ml.

These samples and those prepared in Example 11 (PEG SS bSOD) were stored in dark at 37° C. and analyzed at prescheduled time points for free polyethylene glycol by size exclusion HPLC. Results are reported in Table 1 in units of mg of free PEG per mg of protein. These results are presented graphically in FIG. 1. It can be seen that, even after 6 months (180 days) the vinyl sulfone linkage (PEG vs bSOD) exhibits excellent stability relative the succinate active ester linkage (PEG vs SS bSOD).

TABLE 1

Amount of methoxypolyethylene glycol (PEG) liberated with time at pH 7.0 in Phosphate Buffered Saline (PBS) from PEG VS bSOD (Example 9) and PEG SS bSOD (Example 11)

| Time (days) | PEG from PEG VS bSOD (mg PEG/mg bSOD) | PEG from PEG SS bSOD (mg PEG/mg bSOD) |
|---|---|---|
| 0 | 0.00 | 0.01 |
| 14 | 0.14 | 0.95 |
| 30 | 0.18 | 1.09 |
| 90 | 0.27 | 1.30 |
| 180 | 0.31 | 1.30 |

EXAMPLE 13

Reaction of alpha-[2-(ethenylsulfonyl)ethyl]-omega-methoxy-triethylene glycol with the amine group of N-alpha-p-toluenesulfonyl-L-lysine methyl ester hydrochloride in dimethylformamide.

N-alpha-p-toluenesulfonyl-L-lysine methyl ester hydrochloride (31.6 mg, 0.090 mmol, Sigma Chemical Co.) was dissolved in 1.0 ml of dimethylformamide (DMF). Two drops of triethylamine were added, and then 56.5 mg (0.20 mmol) of alpha-[2-(ethenylsulfonyl)ethyl]-omega-methoxy-triethylene glycol prepared in Example 1 was added. The reaction mixture was stirred at room temperature overnight, and then diluted with water. The product was extracted into three portions of chloroform. The combined chloroform extracts were washed twice with water, dried over anhydrous magnesium sulfate, and the solvent was evaporated to leave 68.6 mg of product. This material was flash chromatographed on silica gel (230 to 400 mesh) using methanol in methylene chloride (5 to 7.5% gradient) to yield 26.4 mg of product identified by proton NMR as a one-to-one adduct of the model lysine to methoxy triethylene glycol divinyl sulfone. The $^1$H NMR (in CDC13) presented the following resonances, consistent with the structure of the product: 7.71 (d, 2H tosyl aromatic), 7.29 (d, 2H, tosyl aromatic), 3.95 (t, 2H), 3.91 (m, 1H, N-CH-C(O)), 3.65 (narrow m, 8H, ethyleneoxy), 3.62 (m, 2H), 3.55 (m, 2H), 3.48 (s, 3H, ester methyl), 3.38 (s, 3H, ether methyl), 3.34 (m, 4H), 3.10 (t, 2H), 2.57 (t, 2H), 2.42 (s, 3H, tosyl methyl), 1.69 and 1.43 ppm (pair of m, 8H, lysyl aliphatic).

EXAMPLE 14

Reaction of alpha-[2-(ethenylsulfonyl)ethyl]-omega-methoxy-triethylene glycol with the amine group of N-alpha-acetyl-L-lysine methyl ester hydrochloride in water.

Two milliliters of a solution of 0.560 g of alpha-[2-(ethenylsulfonyl)ethyl]-omega-methoxy-triethylene glycol, prepared as described in Example 1, in 5.0 ml of 0.1M sodium borate buffer at pH 9.0 was added to 379 mg of N-alpha-acetyl-L-lysine methyl ester hydrochloride (Bachem). The solution was heated and stirred at 37° C. for 16 hours, and the product was then extracted into 2 portions of chloroform, which were combined and dried over anhydrous magnesium sulfate. After filtration, the solvent was evaporated to leave an oil which was flash chromatographed in methanolic methylene chloride using a 5 to 7.5% gradient. The material was identified by mass spectroscopy and by $^1$H NMR as a 1:2 adduct of the model lysine to the alpha-[2-(ethenylsulfonyl)ethyl]-omega-methoxy-triethylene glycol.

EXAMPLE 15

Reaction of alpha-[2-(ethenylsulfonyl)ethyl]-omega-methoxy-triethylene glycol with the amine group in N-alpha-acetyl-L-lysine methyl ester hydrochloride in dimethylformamide.

To a solution of 110 mg (0.462 mmol) of N-alpha-acetyl-L-lysine methyl ester hydrochloride plus 2 drops of triethylamine in 5.0 ml of DMF was added 290 mg (1.03 mmol) of alpha-[2-(ethenylsulfonyl)-ethyl]-omega-methoxy-triethylene glycol, prepared as described in Example 1, in 5 ml of DMF. The solution was stirred at room temperature for two days, then diluted with water and extracted with three portions of chloroform. The combined extracts were washed twice with water and dried over anhydrous magnesium sulfate. After filtration, the solvent was evaporated to leave an oil which was flash chromatographed on silica gel using a 5 to 10% methanol in methylene chloride gradient. The product was separated into two fractions by the chromatography, and the individual fractions were identified by $^1$H NMR and mass spectroscopy to be a mono and a bis adduct of the vinyl sulfone alpha-[2-(ethenylsulfonyl)-ethyl]-omega-methoxy-triethylene glycol to the model lysine amine.

EXAMPLE 16

Reaction of 2,000 dalton alpha-[2-(ethenylsulfonyl)ethyl]-omega-methoxy-poly(oxy-1,2-ethanediyl) with the amine group in N-alpha-p-toluenesulfonyl-L-lysine methyl ester hydrochloride.

To 103 mg (0.0463 mmol) of 2,000 dalton alpha-[2-(ethenyl-sulfonyl)-ethyl]-omega-methoxy-poly(oxy-1,2-ethanediyl), prepared as described in Example 4, dissolved in 1.03 ml of 0.1M sodium borate buffer at pH 8.5 was added 81.3 mg (0.232 mmol) of N-alpha-p-toluenesulfonyl-L-lysine methyl ester hydrochloride. The reaction mixture was stirred at room temperature overnight and then extracted with two portions of chloroform. The combined extracts were washed once with water, dried over anhydrous magnesium sulfate and filtered. The solvent was evaporated, and the residual oil was flash chromatographed on silica gel using 7.5% methanolic methylene chloride to give 48 mg of product, which was shown by $^1$H NMR to be an adduct of the model lysine to the polymeric vinyl sulfone reagent of the invention.

EXAMPLE 17

Alternate synthesis of alpha-[2-(ethenyl-sulfonyl)ethyl]-omega-methoxy-poly(oxy-1,2-ethanediyl) (5,000 dalton molecular weight).

Alpha-[2-(ethenyl-sulfonyl)-ethyl]-omega-methoxy-poly(oxy-1,2ethanediyl) (5,000 dalton molecular weight) is prepared from polyethylene glycol (5,000 dalton) monomethyl ether by first converting it (1 part by weight) to the corresponding alpha-methoxy-omega-chloro-poly(oxy-1,2-ethanediyl) (m-PEG-Cl) by treatment with excess (2 parts by weight) thionyl chloride under reflux overnight. The unreacted thionyl chloride is removed by distillation at reduced pressure, the residual polymer is then taken up in 2 parts of a 1:1 mixture of anhydrous toluene and dichloromethane under anhydrous nitrogen, and most of the solvents plus the last traces of thionyl chloride are removed by distillation under reduced pressure. The residual polymer is taken up in 1 part of anhydrous dichloromethane, filtered, and then treated with 10 parts of anhydrous ether to precipitate the m-PEG-Cl. The chloride is isolated by filtration in the absence of air, washed well with anhydrous ether, and dried to constant weight under reduced pressure. This polymer is then dissolved in warm anhydrous tetrahydrfuran (4 parts) under nitrogen and treated with an excess of mercaptoethanol (1.5 parts) in the presence of anhydrous sodium carbonate. The insoluble salts are removed by filtration, the solvent is removed by distillation under reduced pressure, the residual polymer is taken up in toluene (1 part) and then isolated as above by precipitation with ether. The crude sulfide product is dissolved in 1 part of dichloromethane and treated at room temperature with two equivalents of m-chloroperbenzoic acid to provide the sulfone. After filtration, the polymer is isolated by precipitation as above, and treated again with excess thionyl chloride as above to provide alpha-[2-(chloroethyl-sulfonyl)-ethyl]-omega-methoxy-poly(oxy-1,2-ethanediyl). After removal of the excess thionyl chloride as above, a solution of the polymer in toluene (1 part) is treated with excess 1,5-diazabicyclo[3.4.0]non-5-ene (DBN) to provide the desired alpha-[2-(ethenyl-sulfonyl)-ethyl]-omega-methoxy-poly(oxy-1,2-ethanediyl) in toluene. The solution is filtered, and the polymer is isolated by precipitation with anhydrous ether followed by filtration and thorough washing with ether.

EXAMPLE 18

Preparation of poly(ethylene oxide-propylene oxide) divinyl sulfone adduct.

Poly(ethylene oxide-propylene oxide), 5:1 ratio, available from Polysciences, Inc. with an average molecular weight of 8,750 daltons is treated in tetrahydrofuran with a three fold molar excess of divinyl sulfone in the presence of a catalytic amount of 0.1N NaOH at room temperature under nitrogen followed by work up similar to that described in Example 2 to give a poly(ethyleneoxide-propylene oxide) divinyl sulfone adduct.

EXAMPLE 19

Preparation of a polypropylene oxide divinyl sulfone adduct.

Polypropylene oxide P2000 (available from Dow Chemical, CAS #29434-03-5) with an average molecular weight of 2,000 daltons is treated in tetrahydrofuran with a three fold molar excess of divinyl sulfone in the presence of a catalytic amount of 0.1N NaOH at room temperature under nitrogen followed by work up similar to that described in Example 2 to give a polypropylene oxide divinyl sulfone adduct.

EXAMPLE 20

Preparation of a polypropylene oxide-co-polyethylene oxide divinyl sulfone adduct.

Polypropylene oxide-co-polyethylene oxide Polyglycol 15-200 (from Dow Chemical, CAS #51258-15-2) with an average molecular weight of 2,600 daltons is treated in tetrahydrofuran with a three fold molar excess of divinyl sulfone in the presence of a catalytic amount of 0.1N NaOH at room temperature under nitrogen followed by work up similar to that described in Example 2 to give a polypropylene oxide-co-polyethylene oxide divinyl sulfone adduct.

EXAMPLE 21

Preparation of a 5,000 dalton polyethylene glycol monomethyl ether adduct of bis(vinylsulfonyl)methane: Alpha-[3,5-dithio-3,3,5,5-tetraoxo-hept-6-enyl]-omega-methoxy-Poly(oxy-1,2-ethanediyl).

A solution of 17.23 g (3.307 mmol) of methoxypolyethylene glycol of average molecular weight 5210 daltons (Union Carbide Corporation) is prepared by dissolving the polymer in 172 ml of warm tetrahydrofuran (THF) under a nitrogen atmosphere with magnetic stirring. The solution is cooled to room temperature and then treated with 1.94 g (9.92 mmol) of bis(vinylsulfonyl)methane and then with 12.0 mL of 0.01N aqueous sodium hydroxide solution. The reaction mixture is stirred at ambient temperature for 5 h, then neutralized with 12.0 mL of 0.01N hydrochloric acid solution. The reaction mixture is then filtered, and the filtrate is concentrated on a rotary evaporator with mild heating to remove most of the THF. The residual solution is then diluted with 50 mL of water, washed three times with ether, and then extracted three times with chloroform. The chloroform extracts are then combined, washed with water and dried over anhydrous magnesium sulfate which is subsequently removed by filtration. The solvent is evaporated to leave a solid which is then dissolved in 49 mL of methylene chloride. The product is then precipitated by adding 550 mL of ether. The precipitated solid is filtered, washed with ether and then vacuum dried.

EXAMPLE 22

Preparation of a 5,000 dalton polyethylene glycol monomethyl ether adduct of bis(vinylsulfonylmethyl) ether: alpha-[4-(2-thio-2,2-dioxo-3-butenoxy)-3-thio-3,3-dioxybutyl]-omega-methoxy-poly(oxy-1,2-ethanediyl).

A solution of 17.23 g (3.307 mmol) of methoxypolyethylene glycol of average molecular weight 5210 daltons (Union Carbide Corporation) is prepared by dissolving the polymer in 172 ml of warm tetrahydrofuran (THF) under a nitrogen atmosphere with magnetic stirring. The solution is cooled to room temperature and then treated with 2.24 g (9.92 mmol) of bis(vinylsulfonylmethyl ether) and then with 12.0 mL of 0.01N aqueous sodium hydroxide solution. The reaction mixture is stirred at ambient temperature for 5 h, then neutralized with 12.0 mL of 0.01N hydrochloric acid solution. The reaction mixture is then filtered, and the filtrate is concentrated on a rotary evaporator with mild heating to remove most of the THF. The residual solution is then diluted with 50 mL of water, washed three times with ether, and then extracted three times with chloroform. The chloroform extracts are then combined, washed with water and dried over anhydrous magnesium sulfate, which is subsequently removed by filtration. The solvent is evaporated to leave a solid which is then dissolved in 49 mL of methylene chloride. The product is then precipitated by adding 550 mL of ether. The precipitated solid is filtered, washed with ether and then vacuum dried.

EXAMPLE 23

Preparation of a 3,400 dalton polyethylene glycol divinyl sulfone adduct.

Polyethylene glycol with an average molecular weight of 3,400 daltons, available from Aldrich Chemical Company, Inc., is treated in tetrahydrofuran as a dilute solution with less than one equivalent of divinyl sulfone in the presence of a catalytic amount of 0.1N NaOH at room temperature, under nitrogen, followed by work up similar to that described in Example 2 to give an adduct of the polyethylene glycol with the divinyl sulfone.

EXAMPLE 24

Preparation of a triethylene glycol monobenzyl ether adduct of divinyl sulfone: Alpha-[2-(ethenylsulfonyl)-ethyl]-omega-benzyltriethylene glycol.

To a magnetically stirred solution of 25.0 g (0.166 mol) of triethylene glycol in 500 ml of dry tetrahydrofuran was added 6.66 g (0.166 mol) of a 60 % suspension of sodium hydride in mineral oil. To this was added, over two hours, a solution of 28.47 g (0.166 mol) of benzyl bromide in 50 mL of tetrahydrofuran. After stirring overnight at ambient temperature, the reaction mixture was filtered, and the solvent was evaporated to leave 43.66 g of a tan oil which was fractionally distilled. The fraction boiling at 143° to 149° C. was identified as the desired triethylene glycol monobenzyl ether by $^1$H NMR and mass spectroscopy.

To a magnetically stirred solution of 2.74 g (11.4 mmol) of this triethylene glycol monobenzyl ether in 56 mL of tetrahydrofuran was added 3.44 mL of divinyl sulfone and 3.97 mL of 1N aqueous NaOH solution. After 2 hours at ambient temperature, 3.97 mL of 1N aqueous HCL was added, and the solvent was removed by rotary evaporation. The residual oil was dissolved in chloroform, and the solution was washed twice with water, dried over magnesium sulfate, and filtered. The solvent was removed by rotary evaporation, and the crude product (5.89 g) was purified first by flash chromatography on silica gel using a 2.5 to 5% gradient methanol in dichloromethane to give several fractions which contained the desired product. These were combined, and rechromatographed on silica gel with ether to provide 2.01 g of pure product after removal of the solvent.

Anal. Calc'd for $C_{17}H_{26}O_6S$: C, 56.96; H, 7.31. Found: C, 56.73; H, 7.25.

EXAMPLE 25

Reaction of alpha-[2-(ethenylsulfonyl)ethyl]-omega-benzyltriethylene glycol with the sulfhydryl group in alpha-N-acetyl-L-cysteine as model of cysteine sulhydryl groups found in proteins.

A 2.85 ml (79.6 micromol) aliquot of a 10 mg/mL solution of alpha-[2-(ethenylsulfonyl)ethyl]-omega-benzyltriethylene glycol (prepared as described in Example 24) in 0.1M sodium borate (pH 8.5) buffer was added to 13.0 mg (79.6 micromol) of alpha-N-acetyl-L-cysteine (Aldrich). The solution was magnetically stirred under argon at room temperature, and the reaction was followed by HPLC, using a Dynamax C-8 column with acetonitrile/water as the mobile phase, and monitored at 254 nm. After 35 minutes, the reaction was essentially complete to give a single product which was isolated by preparative HPLC and identified as a 1:1 adduct of the vinyl sulfone to the sulfhydryl group of the model cysteine.

EXAMPLE 26

Reaction of alpha-[2-(ethenylsulfonyl)ethyl]-omegabenzyltriethylene glycol with the amino group in alpha-N-acetyl-L-lysine as a model of a lysine amino group found in proteins.

A 5.30 ml (0.148 mmol) aliquot of a 10 mg/mL solution of alpha-[2-(ethenylsulfonyl)ethyl]-omega-benzyltriethylene glycol (prepared as described in Example 24) in 0.1M sodium borate (pH 8.5) buffer was added to 55.8 mg (0.296 mmol) of alpha-N-acetyl-L-lysine (Aldrich). The solution was magnetically stirred under argon at 37° C., and the reaction was followed by HPLC, using a Dynamax C-8 column with acetonitrile/water as the mobile phase, and monitored at 254 nm. After 19 hours, all of the vinyl sulfone reagent had reacted, and two products had formed in approximately equal amounts. These were isolated (preparative HPLC, combination of like fractions, and evaporation of solvent) and identified as 1:1 and 2:1 adducts of the vinyl sulfone to the epsilon amine of the model lysine.

EXAMPLE 27

Reaction of alpha-[2-(ethenylsulfonyl)ethyl]-omegabenzyltriethylene glycol with the N-terminal amine of the dipeptide L-Ala-L-Ala as model of an unsubstituted N-terminal amino acid often encountered in proteins.

A 1.14 ml (31.8 micromol ) aliquot of a 10 mg/mL solution of alpha-[2-(ethenylsulfonyl)ethyl]-omega-benzyltriethylene glycol (prepared as described in Example 24) in 0.1M sodium borate (pH 8.5) buffer was added to 10.2 mg (63.7 micromol) of the dipeptide L-Ala-L-Ala (Aldrich). The solution Was magnetically stirred under argon at 37° C, and the reaction was followed by HPLC, using a Dynamax C-8 column with acetonitrile/water as the mobile phase, and monitored at 254 nm. After 19 hours, all of the vinyl sulfone reagent had reacted and a single product had formed. This was isolated (preparative HPLC, combination of like fractions, and evaporation of solvent) and identified as a 1:1 adduct of the vinyl sulfone to the terminal amino group of the dipeptide.

EXAMPLE 28

Competitive reaction of alpha-N-acetyl-L-lysine and the dipeptide L-Ala-L-Ala for alpha-[2-(ethenylsulfonyl)ethyl]-omega-benzyltriethylene glycol.

To 580 microliters of a solution of 0.1M sodium borate (pH 8.5) buffer containing 92.4 micromoles each of alpha-N-acetyl-L-lysine and the dipeptide L-Ala-L-Ala was added 3.31 ml of a 10 mg/ml solution (92.4 micromol) of alpha-[2-(ethenylsulfonyl)ethyl]-omega-benzyltriethylene glycol (I, prepared as described in Example 24) in the same buffer. The reaction mixture was stirred at 37° C. for 19 hours at which time HPLC analysis revealed the presence of one adduct of I to the dipeptide (identical by HPLC analysis to that prepared in Example 27) and two adducts of I to the epsilon amine of the lysine (identical to those prepared in Example 26). The ratio, as determined by the relative absorbance at 254 nm by HPLC, of the amount of dipeptide adduct with I to the combined amounts of the two lysine adducts of I was found to be 1.8 to 1 This indicated that the N-terminal amine of the dipeptide reacted with I faster than did the epsilon amine of the lysine under these conditions.

EXAMPLE 29

Competitive reaction of alpha-N-acetyl-L-lysine and N-acetyl-L-cysteine for alpha-[2-(ethenylsulfonyl)ethyl]-omega-benzyltriethylene glycol.

To 300 microliters of a solution of 0.1M sodium borate (pH 8.5) buffer containing 47.8 micromoles each of alpha-N-acetyl-L-lysine and N-acetyl-L-cysteine was added 1.71 ml of a 10 mg/ml solution (47.8 micromol) of alpha-[2-(ethenylsulfonyl)ethyl]-omega-benzyltriethylene glycol (I, prepared as described in Example 24) in the same buffer. The reaction mixture was stirred at 37° C. and monitored by HPLC analysis at 254 nm. In less than 45 minutes all of I had reacted and only the one-to-one adduct of I with N-acetyl-L-cysteine (identical to that prepared in Example 25) could be detected. No change was noted after 3.5 hours. This indicated that the sulfhydryl group of N-acetyl-L-cysteine reacted with I much faster than did the epsilon amine of the lysine under these conditions.

EXAMPLE 30

Stability of alpha-[2-(ethenylsulfonyl)ethyl]-omega-benzyltriethylene glycol to pH 8.5 sodium borate buffer at 37° C. Ten milligrams of alpha-[2-(ethenylsulfonyl)ethyl]-omega-benzyltriethylene glycol (I, prepared as described in Example 24) in 1 ml of 0.1M sodium borate buffer solution was heated at 37° C., and the amount of I remaining was followed by HPLC. After 96 hours, about 95% of the original amount of I (retention time 2.6 minutes) was present together with about 5% of a new material (retention time 11.2 minutes) which was characterized as a monohydrate of I.

Variations and modifications can, of course, be made without departing from the spirit and scope of the invention. Thus, for example, the reagents prepared in the foregoing examples are merely illustrative of the adducts of polyethylene glycol to divinyl sulfone. The reactivities of the residual vinyl sulfone group toward amines on proteins could be increased, for example, by employing bis(vinyl sulfonyl) methane or bis(vinyl sulfonylmethyl) ether.

In view of the results with model studies, it should be possible to functionalize the amine groups on proteins with not only one but two moles of polyethylene glycol reagent. This would further increase the effective hydrodynamic diameter of the modified protein and lead to further increases in circulating half life. In view of the difference in reactivity between the active ester and vinyl sulfone functionality toward lysines, it should be possible to generate reagents of the type:

{Activated ester}-PEG-{vinyl sulfone}.

These reagents should be useful for sequential coupling of two different proteins as follows. Expose Protein #1 to the above double ended reagent so as to react with it rapidly at the active ester end to form a conjugate of the type:

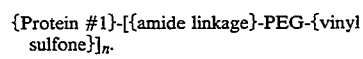

{Protein #1}-[{amide linkage}-PEG-{vinyl sulfone}]$_n$.

This complex could then be treated with a second protein, protein #2, which would react at the vinyl sulfone end to give a mixed conjugate of the type:

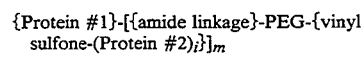

{Protein #1}-[{amide linkage}-PEG-{vinyl sulfone-(Protein #2)$_i$}]$_m$

This could then be further reacted with a PEG reagent, if desired, using single ended reagents of the same or different molecular weight distribution, i.e. the polyethylene glycol vinyl sulfone reagents described in the examples. Thus, for example, this might be useful in the case where protein #1 is catalase and protein #2 is superoxide dismutase.

If the use of polyethylene glycol diol derived reagents is desired for reaction with proteins, it should be possible to arrest the extent of a protein-peg polymerization reaction by the addition of free amino acids to prevent or substantially reduce a tendency to form high molecular weight polymers.

We claim:

1. A reagent comprising a compound having a structural formula:

$$R_4O-(PAO)-E-S(=O)_2-A_a-B_b-C(R^2)=CH_2$$

wherein:

R$_4$ is H or an alkyl or an aralkyl group of 1 to 8 carbon atoms which may be substituted with an alkoxy group of 1 to 3 carbon atoms;

PAO is a polyalkylene oxide having an average molecular weight in the range of 250 to 200,000 daltons;

E is an alkylene group of 1 to 8 carbons, or an alkylenyl group of 2 to 8 carbons or a substituted arylene group of the formula $$-(C_6 \cdot H_h \cdot R^1_i)-$$

where:

each R$^1$ is an electron withdrawing group independently selected from fluoro, trifluoromethyl, and nitro;

i is 0 or an integer from 1 to 4, and h is (4-i);

A is an arylene or an aralkylene group of 6 to 8 carbons which may be unsubstituted or substituted with one or more substituents selected from the group consisting of halogen, methyl, methoxy, and trifluoromethyl; or an alkylene radical of 1 to 8 carbon atoms which may be saturated or unsaturated and which may contain one or more heteroatoms selected from the group consisting of oxygen, nitrogen and sulfur;

a is zero or one;

B is a sulfoxide group;

b is zero or one; provided that a and b are either both zero or both 1; and

R$^2$ is selected from the group consisting of H, F, Cl, CF$_3$, and alkyl groups of 1 to 8 carbon atoms.

2. The reagent of claim 1 wherein A is an alkylene radical of 1 to 8 carbons which may be saturated or unsaturated and which may contain one or more heteroatoms selected from the group consisting of oxygen and sulfur.

3. The reagent of claim 2 wherein b is 0 and a is 0.

4. The reagent of claim 3 wherein R$^2$ is H.

5. The reagent of claim 4 wherein PAO is a polyethylene glycol having a molecular weight in the range of 250 to 200,000 daltons.

6. The reagent of claim 5 wherein the molecular weight is in the range of 250 to 100,000 daltons.

7. The reagent of claim 6 wherein the molecular weight is in the range of 250 to 20,000 daltons.

8. The reagent of claim 7 wherein the molecular weight is in the range of 2,000 to 10,000 daltons.

9. The reagent of claim 8 wherein R$_4$ is CH$_3$.

10. The reagent of claim 9 wherein the molecular weight is in the range of 2,000 to 10,000 daltons.

11. A method for preparing a reagent for bonding a polyalkylene oxide moiety to a polypeptide comprising reacting a polyalkylene oxide having an hydroxyl group and further having an average molecular weight in the range of 250 to 200,000 daltons with a compound having the formula $$X_x-E-S(=O)_f-A_a-B_b-L-D_d$$

where: p1 X is a leaving group;

x is zero or one;

E is an alkylene group of 1 to 8 carbons, or an alkylenyl group of 2 to 8 carbons, or a substituted aryl group of the formula $$G-(C_6 \cdot H_h \cdot R^1_i)-$$

where:

G is a leaving group selected from the group consisting of a nitro group and halogen, or G is a vinyl group, or a haloalkyl group, or a vinyl sulfonyl group, each R$^1$ is an electron withdrawing group independently selected from fluorine, trifluoromethyl, and nitro;

i is 0 or an integer from 1 to 4, and h is (4-i), provided that when x is 1, E is not a substituted aryl group, and when x is zero, E is not an alkylene group;

f is zero, one or two;

A is an arylene or an aralkylene group of 6 to 8 carbons which may be unsubstituted or substituted with one or more substituents selected from the group consisting of halogen, methyl, methoxy, and trifluoromethyl; or an alkylene radical of 1 to 8 carbon atoms which may be saturated or unsaturated and which may contain one or more heteroatoms selected from the group consisting of oxygen, nitrogen and sulfur;

a is zero or one;

B is a sulfur atom, a sulfone group, or a sulfoxide group;

b is zero or one, provided that a and b are either both zero or both 1;

D is a leaving group;

d is zero or one;

when d is 0, L is $$\begin{array}{c} R^2 \\ | \\ -C=CH_2, \end{array}$$

and when d is 1, L is $$\begin{array}{c} R^2 \\ | \\ -C-CH_2-; \\ | \\ R^3 \end{array}$$

R$^2$ is selected from the group consisting of H, F, Cl CF$_3$ and alkyl groups of 1 to 8 carbon atoms; and R$^3$ is selected from the group consisting of H, F and Cl.

12. The method of claim 11 wherein said polyalkylene oxide is a polyaklylene oxide monomethyl ether.

13. The method of claim 12 wherein said polyalkylene oxide monomethyl ether is polyethylene glycol monomethyl ether.

14. The method of claim 11 wherein said compound is divinylsulfone.

* * * * *